(12) United States Patent
Suzuki

(10) Patent No.: US 8,709,468 B2
(45) Date of Patent: Apr. 29, 2014

(54) CLOSED CELL CULTURE SYSTEM

(71) Applicant: Next21 K.K., Tokyo (JP)

(72) Inventor: Shigeki Suzuki, Tokyo (JP)

(73) Assignee: Next21 K.K., Tokyo (JP)

( * ) Notice: Subject to any disclaimer, the term of this patent is extended or adjusted under 35 U.S.C. 154(b) by 0 days.

(21) Appl. No.: 13/707,275

(22) Filed: Dec. 6, 2012

(65) Prior Publication Data

US 2013/0096491 A1 Apr. 18, 2013

Related U.S. Application Data

(63) Continuation of application No. 10/506,045, filed as application No. PCT/JP03/02501 on Mar. 4, 2003, now abandoned.

(30) Foreign Application Priority Data

Mar. 4, 2002 (JP) ................................. 2002-057129

(51) Int. Cl.
*A61F 2/00* (2006.01)
(52) U.S. Cl.
USPC .......................................................... 424/423
(58) Field of Classification Search
None
See application file for complete search history.

(56) References Cited

U.S. PATENT DOCUMENTS

| 4,925,924 A | 5/1990 | Silver et al. |
| 5,358,677 A | 10/1994 | Muth et al. |
| 5,376,376 A | 12/1994 | Li |
| 6,030,358 A | 2/2000 | Odland |
| 6,040,493 A | 3/2000 | Cooke et al. |
| 6,458,109 B1 | 10/2002 | Henley |
| 6,695,824 B2 | 2/2004 | Howard et al. |
| 6,755,807 B2 | 6/2004 | Risk, Jr. et al. |
| 7,004,915 B2 | 2/2006 | Boynton et al. |
| 2001/0021529 A1 | 9/2001 | Takagi |
| 2002/0111576 A1 | 8/2002 | Greene et al. |

FOREIGN PATENT DOCUMENTS

| JP | A 11-46759 | 2/1999 |
| JP | A 2001-507218 | 6/2001 |
| JP | A 2002-200161 | 7/2002 |
| WO | WO 95/31157 A1 | 11/1995 |
| WO | WO 99/07276 A2 | 2/1999 |
| WO | WO 01/87271 A1 | 11/2001 |

OTHER PUBLICATIONS

Oct. 23, 2009 Office Action issued in U.S. Appl. No. 11/785,393.
May 4, 2009 Office Action issued in U.S. Appl. No. 11/785,393.
Jun. 16, 2010 Office Action in corresponding U.S. Appl. No. 10/506,045.

(Continued)

*Primary Examiner* — Allison Ford
(74) *Attorney, Agent, or Firm* — Oliff PLC

(57) ABSTRACT

An object of the present invention is to provide a tissue cell culture system whereby a call tissue can be efficiently and quickly proliferated in vivo and the onset bacterial infection in an injured part can be avoided in the course of a treatment. More specifically, a closed cell culture system (1) characterized in that a defection (2) of a tissue on the body surface or inside the body is tightly sealed to form a closed environment free from the invasion of bacteria, etc. and then a solution appropriate for cell culture is circulated in the tissue defection thus sealed to thereby regenerate the defective tissue; and a method of administering a drug which comprises dissolving a remedy in the perfusion with the use of the above system and thus promoting the treatment of the defection.

8 Claims, 5 Drawing Sheets

(56) References Cited

OTHER PUBLICATIONS

Dec. 24, 2009 Office Action issued in U.S. Appl. No. 10/506,045.
Jun. 26, 2009 Office Action issued in U.S. Appl. No. 10/506,045.
Dec. 19, 2008 Office Action issued in U.S. Appl. No. 10/506,045.
Mar. 25, 2008 Office Action issued in U.S. Appl. No. 10/506,045.
Jul. 13, 2007 Office Action issued in U.S. Appl. No. 10/506,045.
Wang et al., "Spontaneous Cell Sorting of Fibroblasts and Keratinocytes Creates an Organotypic Human Skin Equivalent" Journal of Investigative Dermatology, Apr. 2000, Vo., 114, No. 4, pp. 674-680.

CLOSED CELL CULTURE SYSTEM

This is a Continuation of application Ser. No. 10/506,045 filed Nov. 29, 2004, which in turn is a National Phase of International Patent Application No. PCT/JP2003/002501 filed Mar. 4, 2003, which claims priority of Japanese Patent Application No. 2002-057129 filed Mar. 4, 2002. The disclosure of the prior applications is hereby incorporated by reference herein in its entirety.

CROSS-REFERENCES

The present invention relates to a system which causes cell tissue of an injured part to proliferate in vivo and induces tissue regeneration of the injured part.

BACKGROUND

Injured body parts have conventionally been treated by first removing foreign material and other unnecessary material from the injured part, then disinfecting with a disinfectant or the like and covering the injured part with a wound dressing or the like appropriate for treatment in order to achieve self-regeneration of the skin through cell proliferation. However, self-regeneration of skin is plagued with such intractable problems as time-consuming healing, the occurrence of infections in the injured part and the like.

In order to solve these problems, the method of tissue autotransplantation has recently been applied as a form of regenerative medical engineering, whereby cells near the injured part are collected and proliferated in vitro, and the desired tissue or organ is reconstructed outside the body and returned to the defection. Examples relate to a cell culture system comprising a container for cell proliferation medium and a wound dressing material system (for example, Japanese Patent KOHYO Publication 2001-507218), a cultured skin substitute comprising human fibroblast cells and a product effective for wound treatment (for example, Japanese Patent KOKAI Publication No. 2002-200161) and the like. These methods are all effective when applied to flat tissues, but various problems remain to be solved, including the difficulty of culturing multiple layers of cells (for example, multiple layers of cells including epidermal cells and dermal cells) and the slow speed of cell proliferation.

In the case of thick tissues, moreover, the cell take rate is not particularly high due to the different tissue structures of cells in the body and the difficulty of supplying oxygen or nutrients because of the lack of blood vessels. In addition, there are difficulties in the case of tissues and injured parts with complex three-dimensional solid structures, and it is impossible to prevent infections from occurring during treatment, so problems which existed in the past still remain to be solved.

With the foregoing in view it is therefore an object of the present invention to provide a tissue cell culture system for regenerative medical engineering whereby a cell tissue can be efficiently and quickly proliferated on an injured part or in other words in vivo, and whereby the occurrence of bacterial infections in the injured part can be avoided during treatment.

In order to solve the aforementioned problems, the present inventor perfected the present invention as a result of exhaustive research when he discovered that it was possible to efficiently and quickly regenerate the tissue of a defection in situ by first removing necrotic tissue and other unnecessary material from the opening of the defection, embedding a bioabsorbable material in the defection space as a foundation for cell proliferation, closing the defection from the outside and circulating a solution appropriate for cell culture in the closed space.

SUMMARY

Consequently, the invention according to the first embodiment, which is the basic mode of the present invention, is a closed cell culture system characterized in that a defection of a tissue on the body surface or inside the body is tightly sealed from the outside to form a closed environment free from the invasion of bacteria, and then a solution appropriate for cell culture is circulated in the tissue defection thus sealed to thereby regenerate the defective tissue.

That is, the characteristics of the present invention are that the defection itself is sealed from the outside to form a closed area for perfusion of the solution and prevent infection by bacteria, and that a solution appropriate for cell culture is then circulated in that area, and that continuous disinfection and cell culture can be accomplished by altering the components of the perfusion as appropriate.

Also, because cells ordinarily divide and proliferate by adhering to a particular surface, a foundation to which the cells can adhere is needed for cell proliferation. Cell proliferation is promoted in the present invention by embedding a bioabsorbable material in the defection as such a foundation. Consequently, the present invention according to the second embodiment is a closed cell culture system which promotes regeneration of defective tissue cells by the embedding of a bioabsorbable material in a closed environment in the invention according to the first embodiment.

Examples of such bioabsorbable materials which provided a foundation for cell proliferation include polyglycolic acid fiber, lactic acid glycolic acid copolymer fiber or sponge, glycolic acid caprolactone copolymer fiber, polylactic acid fiber or sponge, lactic acid caprolactone copolymer, polycaprolactone fiber, polydioxane fiber, collagen fiber or sponge, gelatin sponge, fibrin fiber sponge, polysaccharide fiber or sponge, tricalcium phosphate porous beads, calcium carbonate porous beads, hydroxyapatite and the like.

In the closed cell culture system of the present invention, a solution appropriate for cell proliferation is perfused in a cell culture in a closed environment so that cell proliferation can be accomplished effectively. Consequently, the present invention according to the third embodiment is a closed cell culture system whereby the solution appropriate for cell culture in the first and second embodiments is serum isolated from the patient's blood, platelet concentrated serum, a blood preparation, a plasma fraction preparation, a blood protein fraction component solution, a plasma expander, an osmotic pressure isotonic infusion or a cell culture medium.

Moreover, the present invention according to the fourth embodiment is a closed cell culture system whereby a cell proliferation environment appropriate to analgesia and disinfection of the defection and to each tissue to be regenerated is constructed and programmed by changing the components of the circulating solution at each stage of treatment. That is, in order for cell culture in the defection to be effective, the most effective closed environment for cell proliferation needs to established. Consequently, a characteristic of the present invention according to the fourth embodiment is that a cell proliferation environment suited to analgesia and disinfection of the defection and to each tissue to be regenerated can be easily constructed in response to these demands.

Moreover, pH, carbon dioxide partial pressure and oxygen partial pressure of the cell culture environment each vary as the cells are cultured. Consequently, even if a solution of a composition appropriate for cell culture is circulated, the closed environment still needs to be constantly maintained as an optimal environment for cell culture. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. To this end, the present invention according to the fifth embodiment is a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

The present invention according to the sixth embodiment is a closed cell culture system wherein the pressure within the closed environment is continuously or intermittently controlled. That is, the pressure in the closed environment can be varied by means of a pressure maintenance device for example, thus ensuring that the space is suitable for growth of nerve tissue or the like in a positive pressure state, or promoting exudation of bodily fluids in a negative pressure state and thus promoting cell proliferation on the surface of an injured part. By applying negative pressure intermittently, moreover, it is possible to uniformly and efficiently replace the circulating liquid in the closed environment by means of a temporary shrinkage in the volume of the closed environment.

In the case of an extensive and severe burn, a severe loss of body fluid moisture may occur at the injured part. Consequently, when the closed cell culture system of the present invention is used for cell culture of an injured part, the solution which is circulated as the perfusion must have its osmotic pressure adjusted so that the injured surface of the burn can be appropriately maintained. To this end, the present invention according to the seventh embodiment is a closed cell culture system equipped with a circuit for circulating a perfusion the osmotic pressure of which has been adjusted externally.

Moreover, when the closed cell culture system of the present invention is used for cell culture of an injured part, and the injured part involves a relatively deep injury such as nerve cell rupture or the like, less invasive access is desirable when culturing such nerve cells or vascular cells. To achieve such access, a puncture needle can be adopted. Consequently, the present invention according to the eighth embodiment is a closed cell culture system of an aspect wherein a cell culture space is created within an organ or deep inside the body cavity by a combination of a puncture device and a balloon catheter.

That is, proliferation of nerve tissue cells or vascular tissue cells requires that a space be maintained in which they can proliferate. To create such a space the target site in the body is reached by a combination of a puncture needle and a balloon catheter which is passed through the lumen, and the balloon is inflated to create a space suited for proliferation of the target cells. This is also characterized in that it can effectively deposit a bioabsorbable material at the injured part.

It is also possible in the case of the liver, pancreas, kidneys and other parenchymal organs to create a culture space by the same methods and culture the target cells within each organ, thus proliferating within an organ with dysfunction or depressed function cells having better functional structure than cells cultured by external cell culture techniques.

The present invention also provides a method capable of administering a drug which is effective for purposes of cell culture in an injured part. That is, in the closed cell culture system provided by the present invention, the optimal culture components for proliferation of the various cells can be substituted, and cell proliferation factors and vascular proliferation factors which further promote healing can be added to the perfusion and perfused in the defection. Consequently, the present invention according to the ninth embodiment is also a method of administering a drug by dissolving a therapeutic drug in a perfusion using the closed cell culture system according to the first embodiment and thus promoting treatment of a defection. In order to prevent problems due to mixture of incompatible drugs when the therapeutic drug is changed, an intermittent negative pressure cycle is applied to the closed system in such cases so that the perfusion circulating through the cell culture space in the closed environment is actively replaced, allowing the drug solution to be uniformly and efficiently exchanged.

Drugs which can be administered in this case include disinfectants, local anesthetics, anti-phlogistics and analgesics, antibiotic preparations, peripheral vasodilators, various cell proliferation factor preparations, nerve proliferation factor preparations, vascular proliferation factor preparations (or various cell proliferation suppression factor preparations when cancer cells are removed), immunosuppression preparations and the like.

In addition to such drugs, various cell adhesive molecules such as fibronectin, hydronectin and the like can be added to the perfusion. Genes can also be introduced, and examples of such genes include naked DNA, adenovirus vector genes, retrovirus vector genes, liposome encapsulated genes, hydrogel encapsulated genes and the like.

The invention according to the tenth embodiment, which is a different mode of the present invention, is a method of cell transport and proliferation whereby cells from the patient are first collected, cultured and proliferated in vitro, then suspended in a perfusion and returned to the closed culture system via the perfusion system so as to provide therapy by means of a cell culture of the injured part while promoting healing of the injured part in conjunction with culture proliferation and take by tissue cultured in vitro.

KEY

Figure 1:
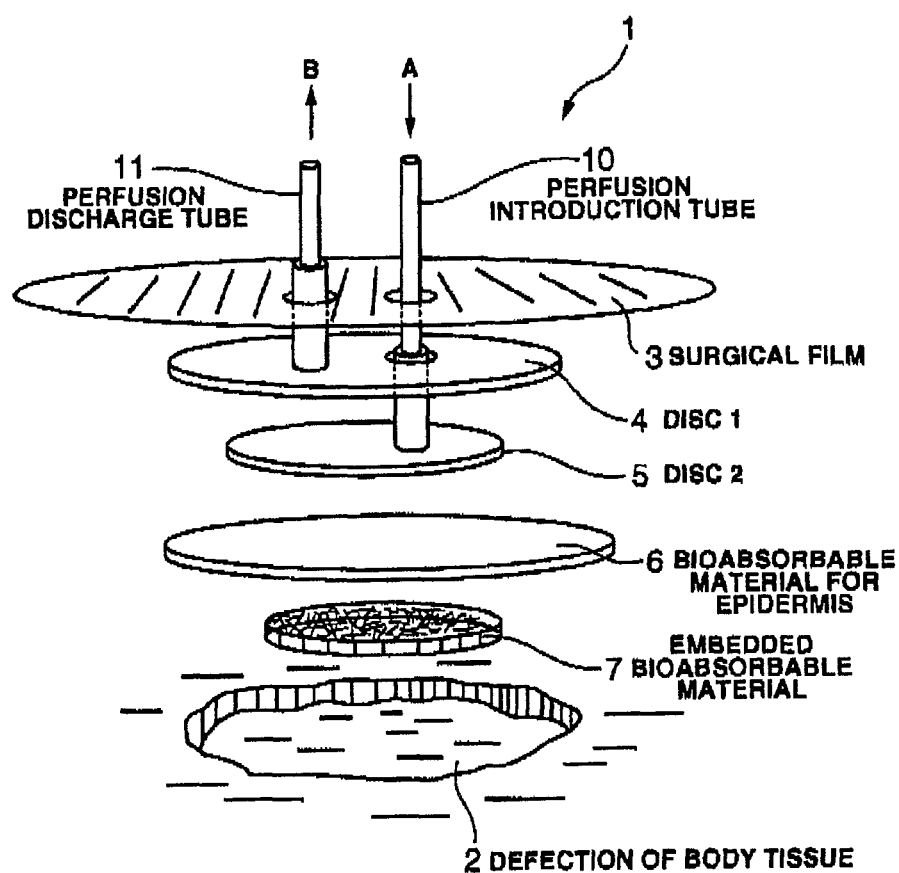
FIG. 1 is a typical simplified exploded view for explaining the closed cell cultured system of the present invention.

1 Closed cell culture system
2 Defection in body tissue
3 Surgical film
7 Bioabsorbable material to be embedded
20 Closed cell culture system
23 Dressing film
24 Double discs
25 Foundation biomaterial
26 Cell proliferation site
30 Puncture needle
32 Balloon
33 Bioabsorbable material
34 Double lumen catheter
40 Perfusion bag
41 3-way stopcock
42 Flow rate regulator
43 Closed cell culture container
44 Pump
45 Discharge
46 Patient
47 pH and gas monitor
48 Gas exchanger
51 Constant pressure continuous suction device

DETAILED DESCRIPTION

The closed cell culture system provided by the present invention is explained in detail below with reference to the drawings.

FIG. 1 is a typical simplified exploded view explaining the closed cell cultured system of the present invention. That is, fundamentally the closed cell culture system (1) provided by the present invention is characterized in that a defection (2) of a tissue on the body surface or inside the body is tightly sealed to form a closed environment free from the invasion of bacteria, etc. and then a solution appropriate for cell culture is circulated in the tissue defection thus sealed to thereby regenerate the defective tissue.

More specifically, in the closed cell culture system (1) provided by the present invention (which in the figure is shown not closed, but in a typical expanded view) a closed environment free from the invasion of bacteria and the like is created by means (3) (a surgical film or other adhesive sheet in the figure) which seals defection (2) of a tissue on the body surface or inside the body, namely by covering and sealing defection (2) of a tissue on the body surface with surgical film (3) to create a closed environment, and a solution appropriate for cell culture is introduced into the closed tissue defection (2) through perfusion introduction tube (10) (in the direction of arrow A in the figure) and perfused to perfusion discharge tube (11) (in the direction of arrow B in the figure).

The perfusion which is perfused through system (1) by perfusion introduction tube (10) soaks for example into epidermal bioabsorbable material (6) via disc 2 (5), from whence it further soaks into embedded bioabsorbable material (7), which is embedded in the tissue defection (2) below, providing the cells in tissue defection (2) with an environment suited for cell proliferation so that cell proliferation can proceed efficiently.

Subsequently, the perfusion which has soaked into embedded bioabsorbable material (7) to fill tissue defection (2) passes through the space between disc 1 (4) and disc 2 (5) and is discharged through perfusion discharge tube (11) on disc 1 (4), completing perfusion.

The two disc layers, disc 1 (4) and disc 2 (5) in the system, may be any with a structure capable of holding perfusion introduction tube (10) and perfusion discharge tube (11), respectively, and they may be formed as a whole with the tubes from a material such as non-water-permeable plastic or the like.

As explained above, by circulating a perfusion into the closed environment of a tissue defection through system (1) of the present invention, it is possible to efficiently promote cell proliferation in the tissue defection by means of a bioabsorbable material which provides a foundation for cell adhesion, and once cell proliferation is complete the bioabsorbable material which forms the foundation is broken down and absorbed and the tissue of the defection is regenerated under sterile conditions.

Figure 2:
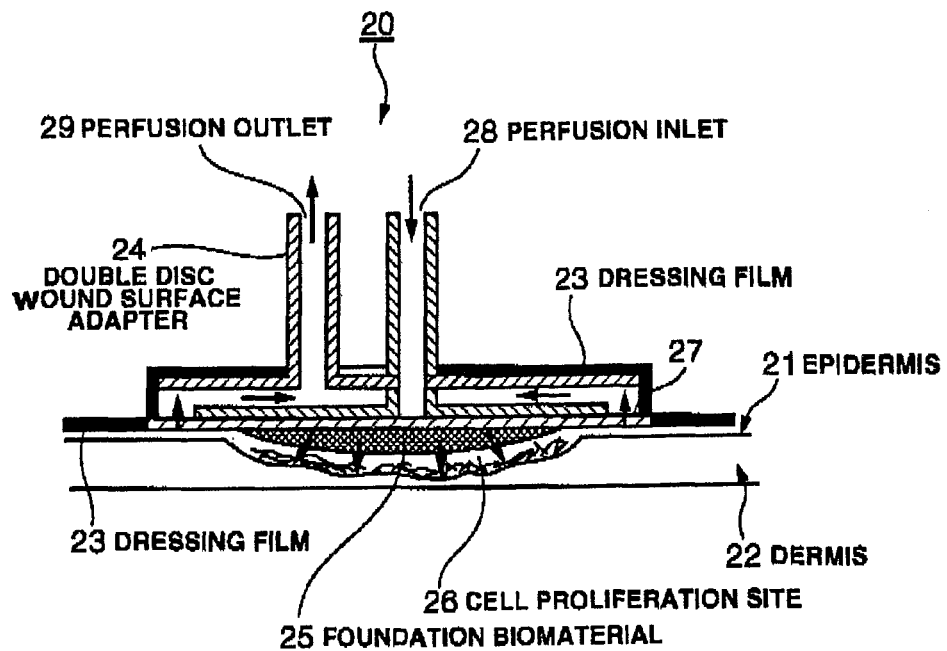
FIG. 2 is a simplified cross-section showing the closed cell culture system of the present invention accessed from the body surface.

FIG. 2 is a simplified cross-section showing the closed cell culture system (20) of the present invention accessed from the body surface. That is, in the case of an external injury, burn, bed sores or other injury, bodily tissue including the epidermis (21) and dermis (22) is defective, and the injured part is exposed at the body surface. In this case, the 2-disc wound surface adapter (24) of the closed cell culture system (20) of the present invention together with a dressing film (23) is applied to the surface of the injury, and a perfusion is perfused. Even in this case, a cell proliferation site (26) having an embedded bioabsorbable material as a suitable foundation biomaterial (25) can be created to promote tissue proliferation in tissues requiring tissue proliferation.

In this case, the perfusion is perfused into the injured part through perfusion inlet (28) in the center of the closed tissue culture system (20) to reach the foundation biomaterial (25) which is a bioabsorbable material, around which it is dispersed. It then passes from the periphery (27) through the gap between the two discs (24), and is expelled as discharge from perfusion outlet (29).

Consequently, invasion of bacteria or the like is prevented because the surface of the injury is sealed, and cell proliferation in the injured part is effectively achieved through the use of a perfusion and a foundation biomaterial.

The size of the closed tissue culture system of the present invention for accessing the surface of the body can be designed at will to match the size of the individual injured part. Consequently, in the case of an extensive burn or the like, a combination of multiple closed tissue culture systems of the present invention having two disc layers can be matched to the size and shape of the burn, and perfusion perfused through each system simultaneously to improve effectiveness as in the case of single use.

In cases such as nerve cell rupture or rupture of vascular tissue in which cell proliferation is performed in an injured part relatively deep in the body, a closed cell culture system employing a puncture needle is employed because less invasive access is desirable. Specifically, a space for proliferation of nerve tissue cells or vascular tissue cells can be created through a combination of a puncture needle and a balloon catheter which is passed through the lumen, after which the foundation biomaterial is deposited in the site expanded by the balloon and perfusion is circulated through a perfusion catheter. The puncture needle in this case is constructed so as to be capable of bending flexibly and of depositing the catheter according to the injured part where cells are to be proliferated.

Figure 3:
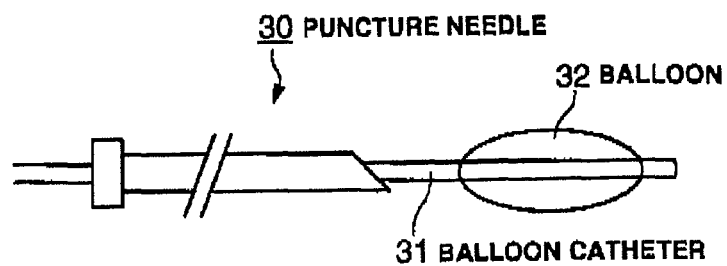
FIG. 3 explains the concept of cell proliferation by the system of the present invention for cell proliferation in the case of nerve cell rupture, which is a deep internal injury.

The concept of cell proliferation in the system of the present invention for proliferating cells in an injured part relatively deep in the body, such as a nerve cell rupture, vascular tissue rupture or the like, is shown in FIGS. 3 through 6. That is, a puncture needle (30) such as that shown in FIG. 3 is inserted through the skin surface, the tip is guided to the part where a space for cell proliferation is to be constructed, a balloon catheter (31) is exposed through the tip of the puncture needle as the tip of the puncture needle is withdrawn, and balloon (32) is inflated.

Figure 4:
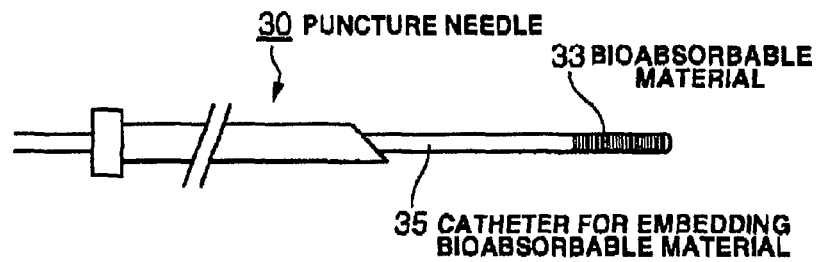
FIG. 4 explains the concept of cell proliferation by the system of the present invention for cell proliferation in the case of nerve cell rupture, which is a deep internal injury.

Next, once a space (space in tissue) for cell proliferation has been created by inflation of the balloon, the balloon is deflated and only the balloon catheter is withdrawn as shown in FIG. 4. A bioabsorbable material (33) which will provide a foundation for cell proliferation is then inserted through the lumen of puncture needle (30). The bioabsorbable material can also be placed via the puncture needle using a catheter already present in the lumen.

Figure 5:
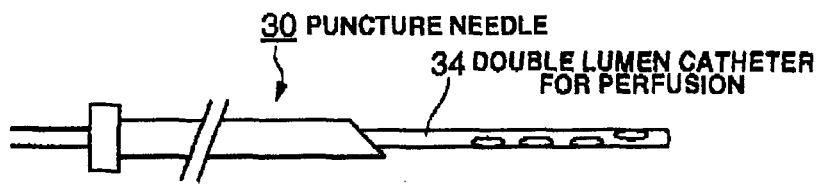
FIG. 5 explains the concept of cell proliferation by the system of the present invention for cell proliferation in the case of nerve cell rupture, which is a deep internal injury.
Figure 6:
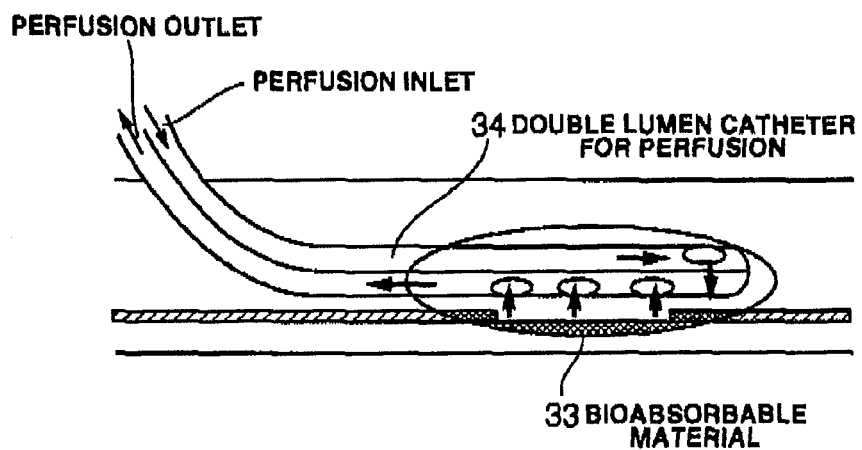
FIG. 6 explains the concept of cell proliferation by the system of the present invention for cell proliferation in the case of nerve cell rupture, which is a deep internal injury.

Once the bioabsorbable material which provides a foundation for cell proliferation has been deposited in the injured part and the catheter for embedding the bioabsorbable material has been withdrawn, a double lumen perfusion catheter (34) for supplying perfusion appropriate to cell proliferation is inserted as shown in FIG. 5, the puncture needle is withdrawn from the body leaving only the perfusion catheter (34), the perfusion inlet (35) and outlet (36) are attached to the perfusion system, and perfusion is initiated. A typical view of this situation is shown in FIG. 6.

As described above, by using the closed cell culture system of the present invention it is possible to tightly seal a defection of a tissue on the body surface or inside the body to form a closed environment free from the invasion of bacteria, and proliferate cells in the defection by circulating a solution appropriate for cell culture in the tissue defection thus sealed, thereby regenerating the tissue.

Figure 7:
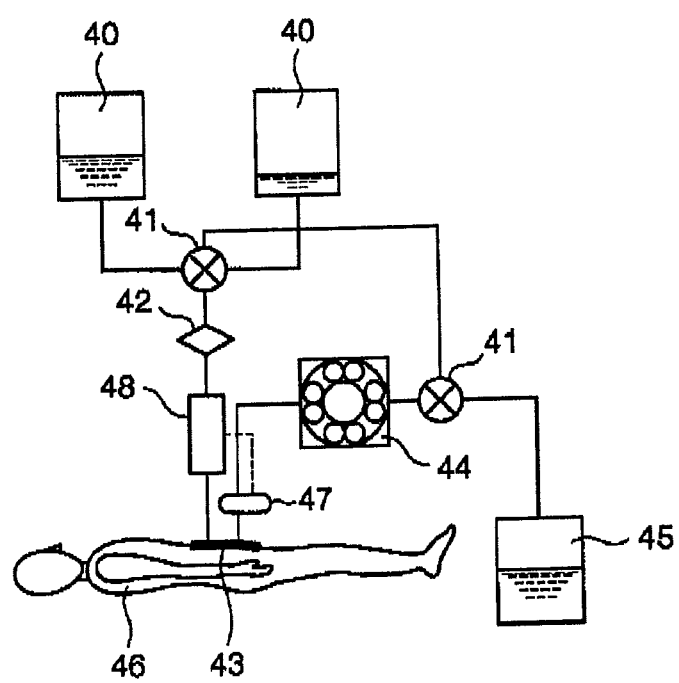
FIG. 7 is a typical explanatory drawing of a case of multiple perfusions circulated by means of the closed cell culture system of the present invention.

Moreover, in the closed cell culture system provided by the present invention it is possible by varying the components of the circulated solution at each stage to construct a cell proliferation environment suited to analgesia and disinfection of the defection and to each tissue to be regenerated. For example, a method which can be used therefor, as shown in the typical simple view of FIG. 7, is to pass multiple types of cell culture perfusion from multiple containers (40) (2 in the figure) through a 3-way stopcock (41) capable of switching the type of perfusion, controlling the flow rate by means of a flow rate regulator (42), and once it has perfused through a closed cell culture system (closed culture container) (43) on the patient (46), discharge the perfused culture liquid via a pump (44) to a discharge container (45).

In this case, the discharge rate of the pump can be controlled using a pressure sensor for example, thus maintaining a constant pressure in the target injured part where cell proliferation is performed.

When multiple perfusions are used, it is possible not only to simply perfuse multiple components appropriate to cell proliferation, but also to perfuse disinfectants for disinfecting a contaminated wound or antibiotics for suppressing proliferation of bacteria at the initial stage, and also to supply perfusion containing various cell proliferation factors, nerve proliferation factors, vascular proliferation factors (or various cell proliferation suppressing factors when cancer cells have been extracted) and the like.

A perfusion containing local anesthetics, antiphlogistics and analgesics, antibiotics, peripheral vasodilators, immune suppressors and the like can also be perfused to achieve effective therapy.

Moreover, the pH, carbon dioxide gas partial pressure and oxygen partial pressure within the culture environment all vary as cell culture progresses. Consequently, the closed environment which is the culture environment should constantly be maintained as an optimal environment for cell culture. To this end, a monitor (47) is provided which measures and monitors physical factors in the culture liquid in the closed environment, namely pH, carbon dioxide gas partial pressure and oxygen partial pressure by means of a sensor, and a gas exchanger (48) installed at the inlet to the culture environment is controlled by means of signals from the monitor, so that the gas partial pressure of the closed environment can be adjusted in real time according to changes in the culture liquid, thus optimizing the cell culture environment.

Figure 8:
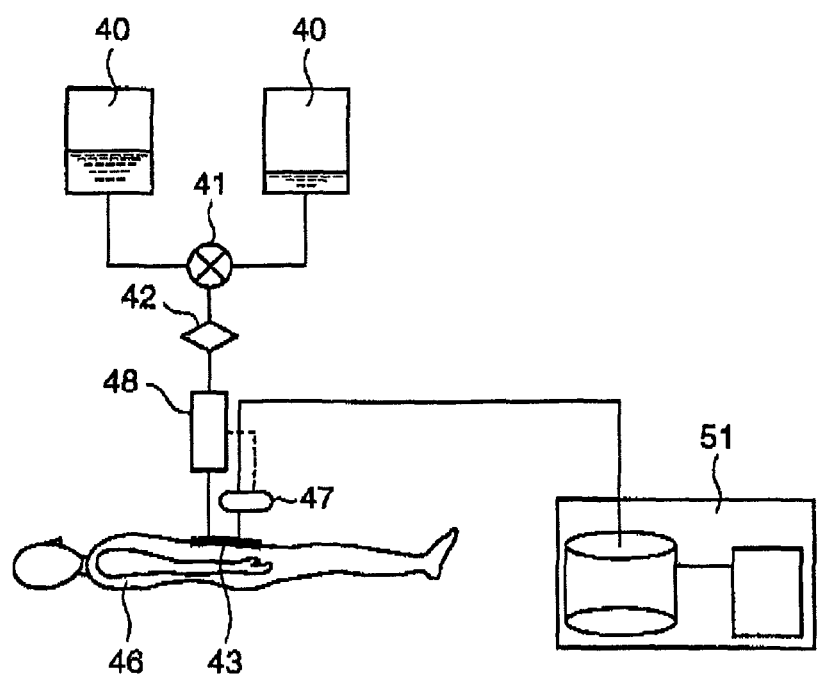
FIG. 8 is a typical explanatory drawing of a case in which a perfusion is circulated by the closed cell culture system of the present invention using a constant pressure continuous suction device, an infusion bag and an infusion tube circuit.

The closed cell culture system provided by the present invention is also capable of perfusing a perfusion appropriate for cell culture using a constant pressure continuous suction device, infusion bag and infusion tube circuit commonly used in hospitals. A typical simple view of this is shown in FIG. 8. The symbols in FIG. 8 are used in the same way as in FIG. 7.

In FIG. 8, the basic concept is the same as that of the system shown in FIG. 7, with the difference that the part which discharges perfused culture liquid to a discharge container via a pump in FIG. 7 is replaced by a part connected to a constant pressure continuous suction device (51) commonly used in hospitals.

As described above, with the present invention once necrotic tissue and other unnecessary matter has been removed from the opening of a defection, a bioabsorbable material which provides a foundation for cell proliferation can be embedded in the defective space and the defection closed off from the outside, and by circulating a solution appropriate for cell culture through the closed space it is possible to efficiently proliferate cells of the defection in situ and regenerate tissue.

EXAMPLES

Specific cases of cell proliferation of the present invention are explained below through examples.

Example 1

Treatment of an Injured Part after Graft Skin Harvesting Surgery

Bleeding from the wound surface after harvesting was quickly stopped using fibrin spray, and the periphery was disinfected. Next, after the concave area was filled with collagen beads an open cell collagen sheet having holes in the middle was formed somewhat larger than the wound surface and placed over the wound surface. A two-layer adapter was also placed on top after being shaped in the same way as the collagen sheet, and a surgical film having openings only at the inlet and outlet of the adapter was applied to form a closed space of the collagen beads and sheet. When there was pain at the harvesting site, the local anesthetic xylocaine was circulated through the closed space together with a plasma preparation containing a mixture of three antibiotics, and three hours later the local anesthetic and antibiotics were stopped and perfusion was switched to basic fibroblast growth factor (bFGF).

Dermal layer tissue was harvested separately, and fibroblast cells which had been carefully float cultured in vitro in fetal cow serum were perfused in exchange for patient serum. Cell transplantation was performed by injecting this opaque cell solution into the closed culture container through the lower 3-way stopcock of a perfusion bag. Next, once cell proliferation of the dermal cells was complete epidermal growth factor (EGF) was substituted for the bFGF, and epidermal cells were cultured until they matched the surrounding skin surface.

Example 2

Neural Reconstruction of a Ruptured Nerve of the Thigh

A puncture needle capable of bending flexibly was inserted so as to reach both ruptured ends of a ruptured nerve. A balloon was selected of a length to reach both ruptured ends of the nerve, a balloon catheter was inserted through the puncture needle and the balloon inflated to create a space between the ruptured ends of the nerve.

A bundle of parallel collagen fibers to provide a foundation for nerve growth in the space was inserted by a catheter contained in a lumen. A fine perfusion catheter was then substituted for the catheter and the puncture needle was withdrawn, leaving only the perfusion catheter.

10-8 moles of nerve growth factor were added to serum obtained from the patient's blood, perfusion was initiated, and a circulating circuit was substituted at the point at which no more air came out.

A slight positive pressure was maintained during perfusion so that the space between the severed ends of the nerve would not collapse. Once the cells had grown sufficiently the perfusion catheter was withdrawn to complete the process.

Example 3

Treatment of a Severe Burn

After skin, dead tissue and the like had been excised from a severe burn on the abdomen, the surface of the burn was covered with a collagen fiber sheet, and a 2-layer perfusion adapter was then attached thereupon. The surface of the wound was first disinfected with an isotonic plasma extender containing povidone-iodine.

A human plasma preparation with osmotic pressure made similar to that of the burn surface was perfused to suppress loss of bodily fluid by the patient from the burn surface. An antibiotic injection was also added to prevent infection, and if the patient complained of pain the local anesthetic xylocaine was injected into the perfusion for pain relief.

Once the patient's condition had stabilized administration of xylocaine and antibiotics was stopped and fibroblast growth factor (bFGF), platelet derived growth factor (PDGF), epidermal growth factor and other cell growth factors were added to the perfusion. Once the epidermis had sufficiently proliferated on the wound the closed cell culture container was removed and the wound surface exposed to air while awaiting further healing.

Example 4

A catheter introducer equipped with a puncture needle was inserted into a rabbit liver under observation by ultrasound tomography. The puncture needle was withdrawn, leaving the introducer sheath, a Fogarty thrombus removal balloon catheter was inserted in its place, and the balloon was inflated to a diameter of about 2 cm to secure a space for cell culture in the liver. The balloon was deflated, the Fogarty catheter was withdrawn, and a teflon tube containing cottony collagen fiber pellets was inserted into the culture space, which was then filled with the collagen fiber pellets. The teflon tube for inserting the collagen was withdrawn, a double lumen for perfusion was placed so that the perfusion openings were in the culture space, and the catheter introducer sheath was withdrawn leaving only the double lumen catheter, which was fixed to the skin by suturing and also by external catheter fixing film.

Serum prepared from the blood of the same rabbit was perfused into the cell culture space while liver cells were cultured inside the rabbit liver for 30 days.

After 30 days of treatment, the rabbit was sacrificed, and autopsy of the treated liver revealed proliferation of liver cells within the collagen fibers.

As described above, an advantage of the closed cell culture system of the present invention is that a defection is closed off from the outside to prevent infection by bacteria or the like, and a solution appropriate for cell culture is circulated in the closed part to efficiently proliferate cells of the defection in situ so that tissue can be regenerated.

Another advantage is that by varying the perfusion, growth factors or therapeutic drugs can be administered to the target site, thus ensuring more effective tissue regeneration.

I claim:

1. A closed cell culture system, comprising:
    a) a bioabsorbable material configured to be embedded within a tissue defect inside a body of a patient to form a cell proliferation site and to be a foundation on which regenerating tissue cells can adhere and proliferate as the tissue defect heals and closes up;
    b) a perfusion introduction tube configured to provide a solution to the bioabsorbable material;
    c) a perfusion discharge tube configured to discharge the solution;
    d) a circuit for circulating the solution, the circuit perfusing the solution within the tissue defect by way of an entrance portion of the perfusion introduction tube, the circuit discharging the solution from the tissue defect by way of an exit portion of the perfusion discharge tube, the solution being appropriate for cell culture; and
    e) a puncture needle and a balloon catheter, the balloon catheter passing through and within the puncture needle and being inflated to create the tissue defect,
    wherein the closed cell culture system is capable of regenerating tissue at the cell proliferation site of the tissue defect.

2. The closed cell culture system according to claim 1, wherein the solution is selected from the group consisting of serum isolated from blood of the patient having the tissue defect, a blood preparation, platelet concentrated serum, a serum fraction preparation, a blood protein fraction component solution, a plasma expander, an osmotic pressure isotonic infusion, and a cell culture medium.

3. The closed cell culture system according to claim 1, further comprising:
    f) a plurality of containers, each of the containers having a different solution;
    g) a stopcock configured to switch connection with each of the plurality of containers, the stopcock being capable of switching from which container the solution is flowing; and
    h) a flow rate regulator configured to control a flow rate of the solution from the stopcock.

4. The closed cell culture system according to claim 1, further comprising:
    f) a sensor, wherein the sensor monitors pH, carbon dioxide partial pressure, and oxygen partial pressure in the closed environment; and
    g) a gas exchanger configured to change gas of the solution, the gas exchanger being automatically controlled by a signal from the sensor, wherein the pH, carbon dioxide partial pressure, and oxygen partial pressure in the closed environment are adjusted by the gas exchanger.

5. The closed cell culture system according to claim 1, further comprising:
f) a constant pressure continuous suction device configured to continuously or intermittently control the pressure inside the closed environment.

6. The closed cell culture system according to claim 1, further comprising:
f) a means for controlling osmotic pressure of the solution, thereby permitting the osmotic pressure of the solution to be adjusted externally.

7. The closed cell culture system according to claim 1, wherein the tissue defect is within an organ of the body.

8. A method of regenerating tissue, comprising:
creating a tissue defect within a human body, the tissue defect being created by a puncture needle and a balloon catheter, the puncture needle being inserted into a human body, the balloon catheter passing through and within the puncture needle and being inflated to create the tissue defect, the tissue defect being a cell proliferation site;
depositing a bioabsorbable material within the tissue defect through the puncture needle;
removing the puncture needle from the body;
setting a perfusion introduction tube to provide a solution to the bioabsorbable material, the solution being appropriate for cell culture;
setting a perfusion discharge tube to discharge the solution;
perfusing the solution within the tissue defect by way of an entrance portion of the perfusion introduction tube; and
discharging the solution from the tissue defect by way of an exit portion of the perfusion discharge tube.

* * * * *